United States Patent

Zamarripa

[11] Patent Number: 6,165,368
[45] Date of Patent: Dec. 26, 2000

[54] METHOD OF CONTROLLING DEPOSITION OF FOULANTS IN PROCESSING EQUIPMENT USED TO PROCESS PRODUCTS STREAMS PRODUCED BY THE DEHYDROGENATION OF ALIPHATIC HYDROCARBONS

[75] Inventor: Robert Zamarripa, Corpus Christi, Tex.

[73] Assignee: Valero Energy Corporation, Houston, Tex.

[21] Appl. No.: 09/136,470

[22] Filed: Aug. 19, 1998

[51] Int. Cl.⁷ .................................................. C02F 1/00
[52] U.S. Cl. .......................... 210/698; 585/833; 585/866; 585/804; 210/773
[58] Field of Search ............................. 585/804, 833, 585/866; 210/698, 773

[56] References Cited

U.S. PATENT DOCUMENTS

| | | |
|---|---|---|
| 2,902,428 | 9/1959 | Kimberlin, Jr. . |
| 2,953,514 | 9/1960 | Wilkins . |
| 3,705,190 | 12/1972 | Bockstahler ........................ 260/486 R |
| 3,844,736 | 10/1974 | Kruis ............................................ 55/32 |
| 4,323,712 | 4/1982 | Imai ....................................... 568/697 |
| 4,401,581 | 8/1983 | Burrows ............................. 252/51.5 A |
| 4,575,568 | 3/1986 | Yuhas, Jr. . |
| 4,608,153 | 8/1986 | Hudson .................................. 208/112 |
| 4,781,820 | 11/1988 | Forte ....................................... 208/333 |
| 5,171,420 | 12/1992 | Forester ............................ 208/48 AA |
| 5,171,916 | 12/1992 | Le et al. ................................. 585/467 |
| 5,200,059 | 4/1993 | Bogdan et al. . |
| 5,243,102 | 9/1993 | Marker . |
| 5,300,715 | 4/1994 | Vora . |
| 5,425,814 | 6/1995 | Krajicek . |
| 5,464,526 | 11/1995 | Saunders . |
| 5,481,060 | 1/1996 | Scott ....................................... 585/867 |
| 5,488,193 | 1/1996 | Mackerer ............................... 585/455 |
| 5,498,810 | 3/1996 | Bogdan et al. . |
| 5,670,026 | 9/1997 | Rutan . |
| 5,672,804 | 9/1997 | Glover ................................... 585/655 |
| 5,792,899 | 8/1998 | Cottrell ................................. 585/827 |
| 5,824,209 | 10/1998 | Arand et al. ........................... 208/135 |
| 5,849,979 | 12/1998 | Kalnes ................................... 585/809 |
| 5,877,361 | 3/1999 | Rojey ...................................... 585/15 |
| 5,942,655 | 8/1999 | Glover ................................... 585/809 |
| 5,988,280 | 11/1999 | Crawford et al. ..................... 166/303 |
| 6,007,701 | 12/1999 | Sherman . |

OTHER PUBLICATIONS

TERGITOL™ NP–10 "Material Safety Data Sheet," J.T. Baker Co.

d–Limonene™ "Material Safety Data Sheet," www.floridachemical.com.

Brochure: "Glycols for Anti–Freezes, Coupling Agents, Humectants, Liquid Coolants, Solvents, Resin Intermediates." Union Carbide. Admitted prior art.

*Primary Examiner*—Chester T. Barry
*Attorney, Agent, or Firm*—Browning Bushman

[57] ABSTRACT

A method for controlling the deposition of foulants such as polynuclear aromatic compounds on the internal surfaces of equipment in a processing train used to process a product stream obtained by dehydrogenating an aliphatic compound containing from 2 to 5 carbon atoms wherein there is introduced into the processing train an effective amount of a liquid solvent having at least one hydroxyl group and a minimum boiling point of about 64.7° C., the solvent being passed through at least a portion of the processing train, after which it is removed from the processing train.

21 Claims, 1 Drawing Sheet

METHOD OF CONTROLLING DEPOSITION OF FOULANTS IN PROCESSING EQUIPMENT USED TO PROCESS PRODUCTS STREAMS PRODUCED BY THE DEHYDROGENATION OF ALIPHATIC HYDROCARBONS

BACKGROUND OF THE INVENTION

1. Field of the Invention

The present invention relates to controlling the deposition or buildup of foulants such as polynuclear aromatic compounds in processing equipment and, more particularly, to processing equipment used to process product streams produced by dehydrogenating aliphatic hydrocarbons.

2. Description of the Prior Art

There are numerous processes for dehydrogenating aliphatic hydrocarbons containing not less than 2 and not more than 5 carbon atoms per molecule. One such process, marketed by UOP as the "Oleflex," process involves dehydrogenating the aliphatic hydrocarbon using a catalyst containing at least one metal or metal compound selected from Group VIII of the Periodic Table.

In particular, the Oleflex process and other dehydrogenation processes are used extensively to dehydrogenate isobutane to produce isobutene, the latter being subjected to an etherification reaction to form methyl tertiary-butyl ether (MTBE), a key component of reformulated gasolines.

In a typical refinery operation to produce MTBE, isobutane is dehydrogenated to produce a dehydrogenated product stream (DPS) containing isobutane and isobutene. Prior to being etherified, the DPS containing the isobutene is passed through a processing train to process the gaseous dehydrogenation product stream to remove any unwanted liquids and other contaminants formed in the dehydrogenation reaction and to compress the gaseous stream.

It is known that in the dehydrogenation of aliphatic hydrocarbons such as isobutane, aromatic compounds are also formed, such aromatic compounds including polynuclear aromatics (PNA). Over and above the fact that the aromatics must be removed from the product stream from the dehydrogenation reaction so as to prevent any unwanted contamination of products produced using the DPS, it is known that certain of the aromatics, particularly the PNA such as anthracene, are prone to deposition on the internal surfaces of equipment in the processing train used to process the DPS. This deposition of the PNA results in fouling of piping, exchangers, valves, and other equipment in the processing train, forcing frequent and expensive shutdowns so that the equipment fouled with the PNA can be cleaned.

SUMMARY OF THE INVENTION

It is therefore an object of the present invention to provide a method for controlling the deposition of PNA and other foulants in equipment in a processing train used to process a product stream recovered from the dehydrogenation of aliphatic hydrocarbons, particularly aliphatic hydrocarbons containing from 2 to 5 carbon atoms.

According to the method of the present invention, an effective amount of a liquid solvent having at least one hydroxyl group and a minimum boiling point of 64.7° C., is introduced into a processing train used to process a product stream obtained from the dehydrogenation of aliphatic hydrocarbons, e.g., a product stream containing isobutane and isobutene. The solvent, once introduced into the processing train, is passed through at least a portion of the processing train and subsequently removed or recovered therefrom. The solvent can be introduced at one or multiple locations in the processing stream, on a continuous or intermittent basis, while the DPS is being processed or during a shutdown or turnaround when no DPS is passing through the processing train.

DESCRIPTION OF THE DRAWING

The single FIGURE is a schematic flow sheet showing the use of the method of the present invention in a typical processing train used to treat the product stream obtained from the dehydrogenation of aliphatic hydrocarbons.

DESCRIPTION OF THE PREFERRED EMBODIMENTS

Figure 1:
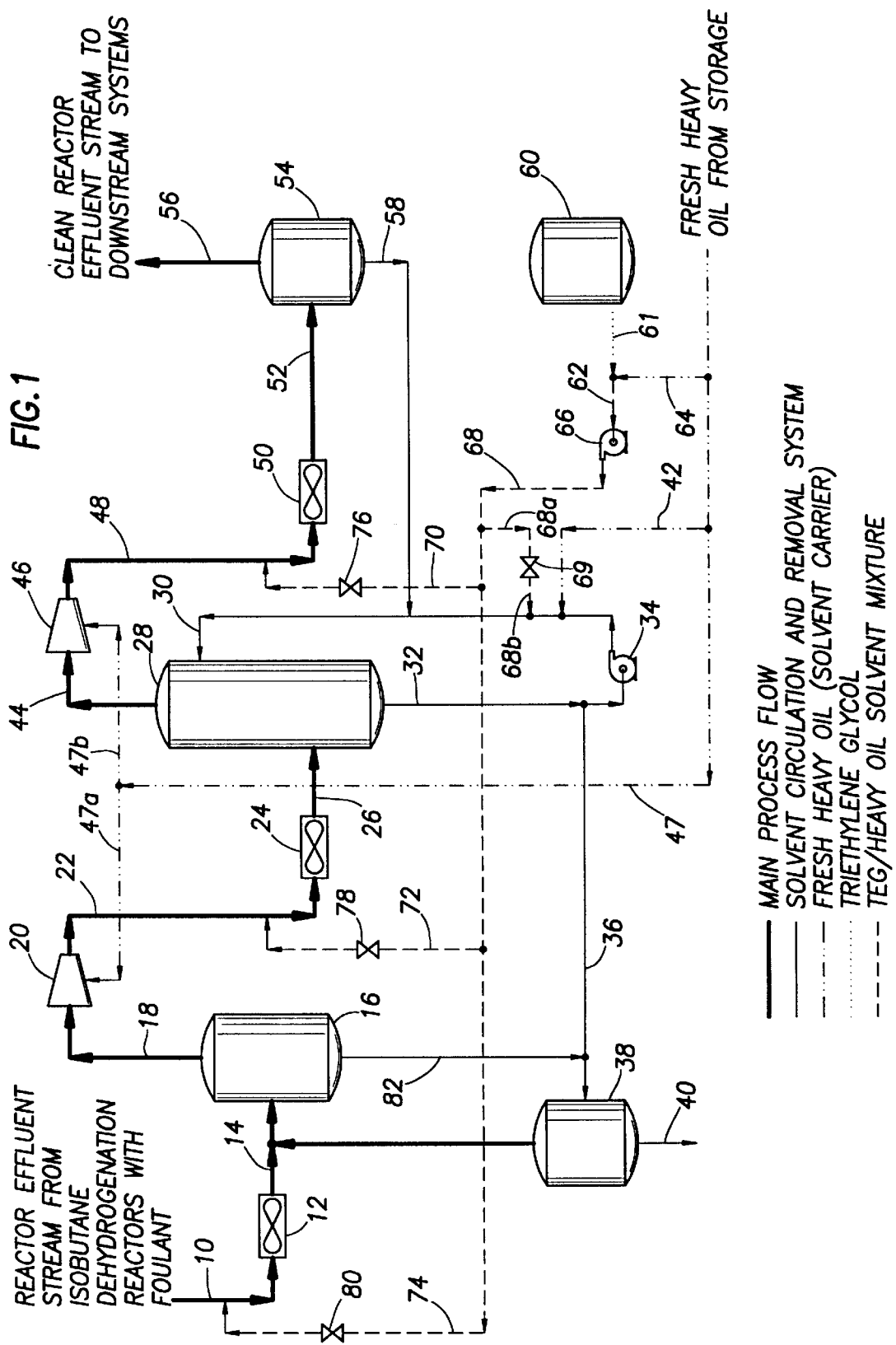

The method of the present invention is applicable to treating any processing train used in the processing of a product stream obtained from the dehydrogenation of an aliphatic hydrocarbon having from 2 to 5 carbon atoms wherein the processing comprises removal of contaminants and foulants formed in the dehydrogenation reaction and/or compression, cooling, and other pretreatment of the DPS. The method finds particular utility in treating processing trains used to process a product stream obtained from the dehydrogenation of isobutane to produce a mixed stream of isobutene and isobutane. However, it will be appreciated that the method is applicable to processing trains used to process product streams obtained from the dehydrogenation of other aliphatic compounds such as ethane, propane, isopropane, and isopentane. In general, the DPS will contain 30–60% (wt) of the corresponding aliphatic hydrocarbon, 30–60% (wt) of the corresponding olefin, less than about 10% (wt) of $H_2$, and generally less than 20% by weight of other by-products, contaminants, foulants, etc.

As noted above, the dehydrogenation of aliphatic hydrocarbons such as those mentioned above typically results in the formation of aromatic compounds including PNA compounds. Typical aromatics formed include compounds having from 9 to 19+ carbon atoms including such compounds as naphthalene, alkyl naphthalenes, indans, quinoline, alkenyl naphthalenes, anthracenes, including m-phenathracenes, pyrenes, etc. These aromatic compounds, particularly certain of the PNA, have a tendency to build up on the internal surfaces of equipment in processing trains used to process the dehydrogenation reaction product prior to the use in subsequent chemical reactions, e.g., etherification. Typically, the aromatics, including the PNA and other high boiling contaminants, are removed by passing the dehydrogenation product stream, e.g., isobutane/isobutene, through an absorber or extractor, where it is contacted with a substantially inert, high boiling absorbing medium, e.g., a hydrocarbon stream. such as, for example, a heavy oil or other typical refinery stream having a boiling point of from about 150° C. to about 430° C. Thus, for example, the normally gaseous dehydrogenation product stream is passed upwardly through a countercurrent scrubber or extractor where it is contacted with the downward passing absorbing medium, the absorbing medium tending to absorb the contaminants, including PNA, present in the dehydrogenation product stream. As noted, it is generally necessary that the dehydrogenation product stream be subjected to several stages of compression prior to being transferred to downstream plants for further chemical processing, e.g., conversion of isobutene into MTBE. Thus, a typical processing train will comprise coolers, compressors, knockout drums, and scrubbers, together with associated piping, valves, and the like. In describing the preferred embodiment of the present invention, and for clarity, only the major sections and interconnections of the processing train are shown. Individual equipment items such as pumps, valves, instruments, heaters, etc., which are not necessary for an understanding of the method of the present invention and which are readily apparent to those of ordinary skill in the art, are not included in the drawing or in the description that follows.

The method of the present invention, which is aimed at controlling the deposition or buildup of PNA and other foulants on the internal surfaces of equipment used in the processing train described above, involves the use of certain selected solvents that can be introduced into the processing train, while the dehydrogenated product stream is being processed, at one or more locations, continuously or on an intermittent fashion or, in the alternative, can be introduced into the processing train when the train is not being used to process a dehydrogenation product stream, i.e., in a turnaround or shutdown. Thus, the term "control" or "controlling" as applied to the deposition or buildup of PNA or other foulants is intended not only to include preventing, retarding, or removing such deposition or build-up while the processing train is handling a dehydrogenated product stream but is also intended to include a cleanup or removal of such depositions or build-ups when the processing train has been shut down for repairs, cleaning, or the like. The method of the present invention finds particular application in the removal of already deposited or built-up PNA or other foulants during operation of the processing train. i.e., when a dehydrogenation product stream is being treated.

The solvents that have been found useful in practicing the method of the present invention are compounds having at least one hydroxyl group and a minimum boiling point equal to that of methanol, i.e., 64.7° C., preferably from 150° C. to 430° C., especially from 150° C. to 300° C., such alcohols being normally liquid at ambient temperatures. Non-limiting examples of such solvents include primary aliphatic alcohols such as methyl, ethyl, propyl, butyl, isobutyl, hexyl, heptyl, octyl, and iso-octyl alcohols: glycols such as ethylene glycol, diethylene glycol, trimethylene glycol, triethylene glycol (TEG), hexylene glycol, 2-ethyl-1,3-hexanediol, 1,5-pentanediol, etc. Additionally trihydric and other polyols such as glycerol, polyethylene glycols, propylene glycols, etc., can also be employed. Particularly preferred are glycols or diols having from 3 to 8 carbon atoms. The hydroxy solvents used can include compounds that are only alcohols or that, in addition, contain other groupings and/or atoms, e.g., ether linkages. It will be recognized that mixtures of various of the hydroxyl-containing compounds can be used and that the specific alcohol or mixture thereof will depend upon the nature of the dehydrogenated product stream being treated. It is only necessary, to be useful in the method of the present invention, that the alcohol have a minimum boiling point of 64.7° C., be non-reactive with the desired components of the dehydrogenated product stream, be a solvent for the PNA and/or other foulants, and be separable from the dehydrogenation product stream, preferably by simple techniques such as fractionation, cooling, flashing, etc., to avoid or at least minimize any carryover of solvent into downstream processes.

As used herein with reference to the alcohol used in the method of the present invention, the term "solvent" is not intended to mean that the alcohol necessarily is capable of forming a true solution of any or all of the PNA or other foulants that may be built up on the internal surfaces of the equipment in the processing train. Rather, the term "solvent" as used in the context of the method of the present invention means the ability of the absorbent to retard, prevent, dislodge, or remove, by whatever action is occurring, e.g., dissolution, the build-up of PNA and other foulants from the internal walls of the equipment. While undoubtedly this action involves, to some extent, dissolution of PNA and perhaps other solids that are built up on the internal surfaces of the equipment, it does not mean that all of the PNA or other foulants are soluble in the alcohol used in the method of the present invention. Indeed, there are literally hundreds of by-product compounds formed in the dehydrogenation reaction, albeit in extremely small or even trace amounts. It could be postulated that it is these trace components that form the focal point for deposition of PNA and other foulants and that these unknown, trace components, which readily adhere to the surfaces of the equipment, in effect, serve as "deposition sites" for PNA and other foulants. In any event, the term "solvent" as used herein with respect to preventing, retarding, or removing build-up of foulants on the internal surfaces of the equipment used in the processing train is intended to include actual salvation of at least certain species of the foulants, as well as concomitant dislodging of such foulants from such surfaces, matter not the mechanism.

While it is possible to introduce the alcohol solvent in a neat form or in admixture only with other alcohol solvents useful in the method of the present invention, it is generally less expensive and more convenient to use a liquid carrier for the alcohol solvent. Generally speaking, the liquid carrier will comprise a liquid hydrocarbon that also acts as the absorbing medium described above and that exhibits no deleterious effect vis-á-vis the dehydrogenated product stream and will usually comprise one of several hydrocarbon streams commonly found in refinery operations. Thus, various hydrocarbon streams boiling in the range of from about 150° C. to about 430° C. can be used. Non-limiting examples of such carriers include heavy oils, which are generally heavier fractions recovered from catalytic cracking operations. For example, a heavy oil recovered from a catalytic cracking operation having an initial boiling point of 200° C. and an end boiling point of 370° C. has been found to useful as a carrier, as well as an absorbing medium, in the method of the present invention. It will be apparent that the carrier can comprise a number of different hydrocarbons or hydrocarbon streams, the only requirement being that it not react with the alcohol solvent or the desired components of the dehydrogenation reaction product in the processing train. Additionally, the carrier should be one that, like the alcohol solvent, can be separated from the dehydrogenated reaction product, preferably by methods such as fractionation, cooling, etc., again to avoid carryover downstream of the processing train.

Reference is now made to the accompanying drawing for an illustration of the use of the method of the present invention. While the following description illustrates the use of the method of the present invention with reference to a specific hydrogenation product stream and a specific alcohol, as indicated above, it is to be understood that it is not so limited.

With reference now to the single FIGURE, a dehydrogenation product stream comprising isobutane, isobutene, and foulants (aromatics, including PNA), and other by-products of the dehydrogenation reaction, is introduced into the processing train via line 10 and passes through a first-stage cooler 12 into line 14 and then into a compression suction drum 16. The overhead from the compression suction drum 16 passes via line 18 to the intake of a first-stage compressor 20. The compressor discharge stream from compressor 20 passes via line 22 into a second-stage cooler 24, the cooled stream exiting cooler 24 via line 26. The compressed, cooled dehydrogenation product stream then enters liquid absorber 28, which can be of the packed or plate type but generally is a countercurrent, plate tower. The dehydrogenation reaction product flows upwardly through absorber 28 countercurrent to an absorbing medium (as described above) introduced into the upper portion of absorber 28 via line 30. In absorber 28, certain gases, liquids, PNA, and other such contaminants in the dehydrogenation product stream are absorbed by the absorbing medium, which is received from absorber 28 through line 32, a portion of the absorbing medium being recycled via pump 34 back to line 30 to absorber 28. As can also be seen, a purge stream of absorbing medium is removed from line 32 via line 36 and transferred to a solvent removal drum, the solvent in solvent removal drum 38 being removed via line 40 for further processing in the refinery operations. A make-up stream of fresh absorbing medium is introduced into line 30 via line 42 from a suitable storage facility not shown.

The overhead from absorber 28, largely freed of liquids, PNA, and the like, passes via line 44 to the intake of a second-stage compressor 46. As can be seen, the absorbing medium is also introduced into first- and second-stage compressors 20 and 46, respectively, via lines 47, 47a, and 47b. The compressor discharge stream from second-stage compressor 46 passes via line 48 to a third-stage cooler 50. The effluent from third-stage cooler 50 passes via line 52 into a knockout drum 54, a substantially clean stream of dehydrogenation reaction product being removed from drum 54 as an overhead fraction via line 56. The bottoms fraction from drum 54 is removed via line 58 and led to line 30, i.e., subsequently back to absorber 28 and eventually, via purge line 36, to solvent removal drum 38.

What has been described above is basically a processing train comprising several stages of cooling and compression designed to remove contaminants, including liquid aromatics, PNA, etc., from the dehydrogenation product stream entering the process train via line 10 to produce a substantially liquid-free dehydrogenation product stream exiting the processing train via line 56. As noted above, while absorber 28 is effective at removing at least some, and generally a substantial amount, of the foulants, e.g., PNA, it does not eliminate carryover of all of the PNA or other foulants in the overhead stream from the absorber. Furthermore, the foulants entering the processing train via line 10 can deposit on the internal surfaces of the processing train between line 10 and absorber 28, even assuming that absorber 28 is completely effective in eliminating all of the foulants from the stream entering absorber 28. Prior to the present invention, it was found that, indeed, PNA and other foulants were being carried over through the second-stage compressor 46 and were fouling third-stage cooler 50, causing frequent shutdowns to enable cooler 50 to be cleaned. The fouling of the third-stage cooler results in an increased pressure drop across the cooler and a higher than desired exit temperature of the cooler effluent. Higher cooler effluent temperatures are undesirable since it results in more downstream carryover of contaminants, which can have deleterious effects on downstream processing, e.g., reduced production of MTBE, off-color MTBE, etc. To eliminate this problem, as well as eliminate the deposition of PNA on the internal surfaces of equipment forming the processing train upstream of absorber 28, triethylene glycol (TEG) from storage drum 60 via line 61 is admixed with fresh heavy oil (absorber medium) from line 64 to form a mixture of TEG and absorbing medium, which is pumped by pump 64 from line 62 into line 68 for subsequent introduction into the processing train at various points as described hereafter.

As can be seen, there are three branch lines from line 68, namely, line 70, line 72, and line 74. All of lines 70, 72, and 74 are disposed just upstream of the inlets of third-stage, second-stage, and first-stage coolers 50, 24, and 12, respectively. Line 70 is provided with a valve 76 while line 72 is provided with a valve 78, line 74 being provided with a valve 80. It will be apparent that the mixture of absorbing medium and TEG, by selective operation of valves 76, 78, and 80, can be introduced into the inlet(s) of any one or any combination of coolers 12, 24, and 50. Thus, the absorbing mediun/TEG mixture can be introduced only into the inlet of cooler 12, valve 80 being open, while valves 78 and 76 are closed. Alternatively, the absorbing medium/TEG mixture can be introduced into the inlet of cooler 50, valve 76 being open, valves 78 and 80 being closed. In addition to introducing the absorbing medium/TEG mixture into the coolers, it can also be introduced directly into absorber 28 via line 68a, valve 69, and line 68b. Indeed, it will apparent that there are numerous points of introduction of the absorbing medium/TEG mixture into the processing train that can be used to effectively reduce the deposition of PNA and other foulants on the internal surfaces of the equipment forming the processing train and through which the absorbing medium/TEG heavy oil mixture flows.

In cases wherein the TEG is introduced into the processing train, after passing through at least a portion of the processing train, and perhaps the entire processing train, it is ultimately removed from the processing train. For example, at least a portion of the TEG introduced into the inlet of cooler 12 would be removed in compressor suction drum 16 and returned via lines 82 and 36 to the solvent removal drum 38. In like fashion, TEG introduced into cooler 24 via line 72 and valve 78 would be at least partially removed in scrubber 28 and at least a portion returned to solvent removal drum 38 via line 36. Lastly, essentially all of any TEG introduced upstream of compressor knockout drum 54 will be recovered in knockout drum 54 and ultimately transferred to solvent removal drum 38. As noted, a purge stream 36 from the recycle loop to absorber 28 would also remove at least a portion of the TEG in absorber 28, which would be transferred to solvent removal drum 38 and then passed via line 40 for recovery or other usage.

Although as shown above, the TEG is introduced just upstream of the coolers, i.e., at the inlet of the coolers, it will be apparent to those skilled in the art that the TEG can be introduced into the processing train at other single or multiple locations. However, introduction of the TEG into the inlet of the coolers, particularly the third-stage cooler 50, is desirable since it is at that point that PNA and other foulants are most likely be deposited.

The amount of alcohol solvent introduced into the processing train will be an amount sufficient to control PNA (foulant) deposition on the internal surfaces of the processing equipment used for processing the dehydrogenated product stream. Obviously, a sufficient amount will depend upon numerous factors, including the degree to which PNA and other foulants are being made in the dehydrogenation reaction, the rate that the PNA and other foulants are being deposited on the internal surfaces of the system making up the processing train, the size of the processing train, flow rates through the processing train, etc. In general, however, the amount of alcohol absorbent solvent introduced will be just that amount that is necessary to prevent any substantial deposition of an amount of PNA or other foulant sufficient to interfere to any significant degree, with the operation of the equipment forming the processing train, e.g., an amount sufficient to prevent any significant fouling of any of the coolers. Additionally, the amount of alcohol solvent introduced will depend upon the particular alcohol solvent(s) used. In general, and in the case when the alcohol solvent is being admixed with the carrier, e.g., the heavy oil, it has been found that a weight ratio of alcohol solvent to carrier of from about 1:300 to about 1:2 is sufficient. This is the case when the processing train is being used to process the dehydrogenated product stream and the solvent is being added to the on-line operation. In cases where no such processing is being conducted in the processing train, i.e., during a turnaround, it may be more desirable and cost effective to use only alcohol solvent or to use a much higher ratio of alcohol solvent to heavy oil ratio (absorbing medium).

As noted above, the feed of the alcohol solvent into the processing train can be on an intermittent or continuous basis while the processing train is operating, i.e., processing the dehydrogenation reaction product. Generally speaking, the alcohol solvent per se will be fed to the processing train at a rate of from about 20 to about 100 lbs./hr. per 300,000 lbs./hr. of dehydrogenation reaction product fed to the processing train. This rate, of course, will depend upon the particular alcohol solvent chosen, the nature of the dehydrogenation reaction product, and other such variables mentioned above.

The method of the present invention has proved to provide unexpected results under actual plant conditions, as shown by the following, non-limiting examples.

EXAMPLE 1

In this case, the dehydrogenation reaction product feed rate to the processing train, substantially as shown in the FIGURE, was approximately 320,000 lbs. per hour, the DPS containing 44.4 wt % isobutane; 38.6 wt % isobutene; 5.7 wt % hydrogen; about 11.2 wt % by-products, e.g., methane, propane, etc.; and approximately 0.1 wt % by-products (foulants). A mixture of one part by weight TEG (98% by weight) to two parts by weight a refinery hydrocarbon stream (absorbing medium) having an initial boiling point of 200° C. and an end boiling point of 370° C. was injected into the processing train at the inlet of what can be considered cooler 50, as shown in the figure. The injection rate of the mixture was approximately 1500 lbs. per hour. The mixture was introduced into the cooler, i.e., cooler 50, in three different 25- to 60-minute segments at 1.5 hours apart. An immediate impact on the performance of the cooler was observed. Pressure surveys conducted prior to injection of the absorbing medium/TEG mixture indicated a 14–15 psi pressure drop across the cooler. After the injection procedure, the pressure drop was reduced to 9–10 psi. Further, the outlet temperature on the cooler had dropped from 55° C. to 49° C., this temperature occurring during the heat of the day (~36° C.). After allowing the process to line out, discharge pressures from the processing train were increased slightly to take advantage of the reduced pressure drop in the cooler. It was noted that the 24-hour average production rate of MTBE produced from the clean dehydrogenation reaction product stream leaving the process train via line 56 had increased from 16,900–17,200 BPD to 17,650+BPD.

EXAMPLE 2

In a second plant test, the same mixture and feed rate as used in Example 1 were employed. Essentially, the procedure of Example 1 was followed, with the exception that the absorbing medium/TEG mixture was continuously fed to the cooler. It was noted that outlet temperatures on the cooler dropped from approximately 53° C. to less than 43° C. Again, this temperature was measured during the heat of the day, the ambient temperature being approximately 36.1° C. Additionally, a pressure drop across the cooler had been reduced to 3–4 psi as compared with the 14–15 psi pressure drop initially seen across the cooler (see Example 1). Twenty-four-hour average production rates of MTBE exceeded 17,800 BPD following this second cleaning. It is to be noted that these higher MTBE production rates, while largely affected by reduced pressure drop and decreased temperature in the cooler, were also the result, to some extent, of modifications in the dehydrogenation process unit.

At no time following intermittent or on-line injection of the absorbing mediun/TEG mixtures were any problems experienced in the MTBE process unit with respect to product color or quality. Indeed, it was noted that product color improved as the coolers were cleaned. This is obviously due to lower cooler outlet temperatures, which lessened the amount of carryover of contaminants to downstream systems. Surprisingly, when using the method of the present invention such that the coolers were cleaned of any built-up PNA or other foulants, MTBE production was maintained at 17,700+ BPD during a two-day period when the plant facility experienced the highest ambient temperature ever recorded (roughly 41–43.5° C.). Normally, these ambient temperatures would have resulted in 14,000–15,000 BPD MTBE production rates.

As can be seen from the above, actual plant results, the method of the present invention provides a dramatic solution to the problem of eliminating, or at least severely curtailing the build-up and subsequent fouling in equipment in a processing train used to process a dehydrogenated product stream, e.g., a product stream containing isobutane and isobutene.

The foregoing description and examples illustrate selected embodiments of the present invention. In light thereof, variations and modifications will be suggested to one skilled in the art, all of which are in the spirit and purview of this invention.

What is claimed is:

1. A method for controlling the deposition of polynuclear aromatic compounds on the surfaces of equipment in a processing train used to process a product stream obtained from the dehydrogenation of aliphatic hydrocarbons having from 2 to 5 carbon atoms, comprising:

introducing into said processing train during processing of said product stream an amount of a liquid solvent sufficient to control deposition of said polynuclear aromatic compounds on said surfaces, said liquid solvent having at least one hydroxyl group and a boiling point within the range of from 150° C. to 430° C., and being non-reactive with the desired components of the dehydrogenated product stream;

passing said solvent through at least a portion of said processing train; and recovering said solvent from said product stream to minimize carryover of said solvent into downstream processes.

2. The method of claim 1 wherein said liquid solvent comprises a polyol.

3. The method of claim 2 wherein said polyol comprises a glycol.

4. The method of claim 3 wherein said glycol comprises triethylene glycol.

5. The method of claim 1 wherein said product stream comprises a mixture of isobutane and isobutene.

6. The method of claim 1 wherein said processing train contains at least one cooling zone having an inlet and an outlet and said solvent is introduced substantially at the inlet of said at least one cooling zone.

7. The process of claim 6 wherein said processing train contains a plurality of said cooling zones and said solvent is selectively introduced into more than said one cooling zone.

8. The method of claim 7 wherein said solvent comprises a polyol.

9. The method of claim 8 wherein said polyol comprises a glycol.

10. The method of claim 9 wherein said glycol comprises triethylene glycol.

11. The method of claim 6 wherein said solvent comprises a polyol.

12. The method of claim 11 wherein said polyol comprises a glycol.

13. The method of claim 12 wherein said glycol comprises triethylene glycol.

14. The process of claim 1 wherein said processing train contains at least one compression zone.

15. The process of claim 14 wherein said processing stream contains a plurality of compression zones.

16. The process of claim 1 wherein said solvent is continuously introduced into said processing train during processing of said product stream.

17. The method of claim 1 wherein said solvent is introduced into said processing train at multiple locations.

18. The method of claim 1 wherein said solvent is introduced in admixture with a liquid carrier.

19. The method of claim 18 wherein said liquid carrier comprises a liquid hydrocarbon mixture having a boiling point within the range of from 150° C. to 430° C.

20. The method of claim 1 wherein the solvent is selected from the group consisting of primary aliphatic alcohols, ethylene glycol, diethylene glycol, triethylene glycol, hexylene glycol, 2-ethyl-1,3-hexanediol, 1,5-pentanediol, glycerol, polyethylene glycol, propylene glycol, and mixtures thereof.

21. The method of claim 1 wherein said solvent is intermittently introduced into said processing train during processing of said product stream.

* * * * *